United States Patent [19]

Wheeler

[11] 4,226,025
[45] Oct. 7, 1980

[54] SURGICAL CALIPER

[76] Inventor: Michael R. Wheeler, 1720 Andres Ave., Torrance, Calif. 90501

[21] Appl. No.: 17,400

[22] Filed: Mar. 5, 1979

[51] Int. Cl.³ .............................................. G01B 5/02
[52] U.S. Cl. ................................ 33/148 E; 33/143 C; 33/174 D; 128/774
[58] Field of Search .............. 33/1 V, 143 C, 148 R, 33/148 E, 148 F, 149 R, 174 D; 128/774

[56] References Cited

U.S. PATENT DOCUMENTS

| | | | |
|---|---|---|---|
| 466,986 | 1/1892 | Van Roden | 33/148 E |
| 1,380,269 | 5/1921 | Sumersille | 33/148 E |
| 1,528,273 | 3/1925 | Shwed | 33/148 E |
| 1,626,540 | 4/1927 | Kimura | 33/148 E |
| 3,740,779 | 6/1973 | Rubricuis | 33/174 D |

Primary Examiner—Richard R. Stearns
Attorney, Agent, or Firm—Ian C. McLeod

[57] ABSTRACT

A caliper which is especially constructed for measuring the length, width, area and/or volume of living parts of mammals during surgery, without injuring the parts, particularly inside a body cavity is described. The caliper includes a pair of long straight arms which are approximately parallel in a closed position and which pivot apart in a scissors movement in order to position the body part between the distal ends of each of the arms used for measuring. The other ends of the arms are connected to a pivot means and to a handle provided by extensions from the arms and the pivot means. Adjacent the distal ends of the arms, precisely measured and spaced apart reflecting means, such as ridges or grooves, are provided which reflect a surgery light when the arms are inside the body cavity and preferably having contrasting colored shiny tips at the distal ends. The caliper includes a scale with index marks associated with the extensions of the arms from the pivot means such that at least the linear distance between the arms and thus the length or width of an anatomical part inside the body cavity can be measured using the marks.

12 Claims, 7 Drawing Figures

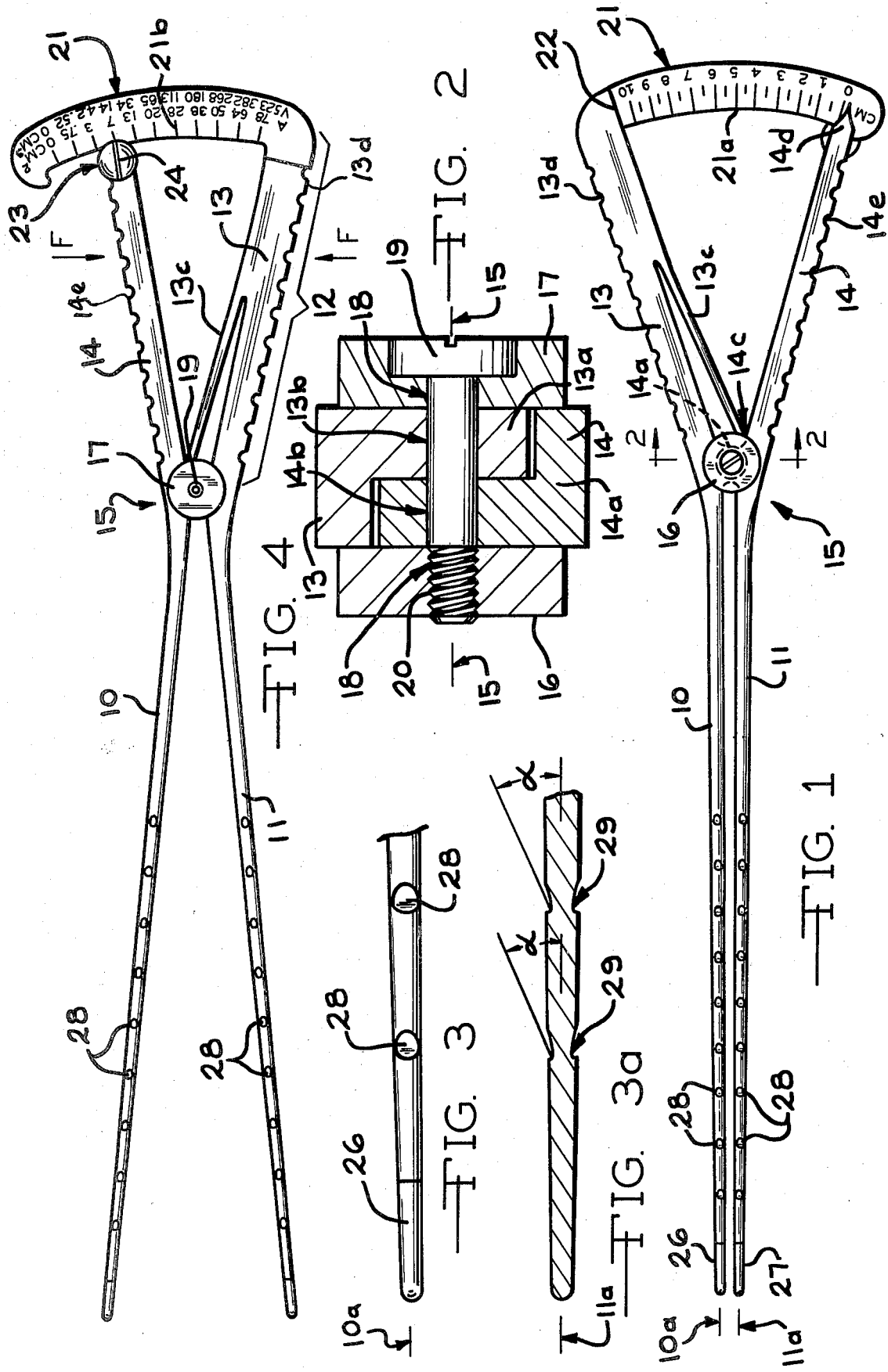

SURGICAL CALIPER

DESCRIPTION OF THE INVENTION

The present invention relates to a surgical caliper. The present invention particularly relates to a caliper adapted to measuring living parts inside a body cavity without injury to the parts.

PRIOR ART

The problem faced by the prior art is to standardize and facilitate surgical techniques, and to document surgical procedures using an instrument for making the following primary, direct surgical measurements: (1) determination of rectilinear dimensions of structures, both anatomical and pathological, within a confined surgical field such as inside a body cavity. As an example there is a problem in measuring the length of an anastomotic suture line or the lengths of arteries, bowel, bones and nerves in repairing, grafting, bypass and orthopaedic operative procedures deep within and incision; (2) rapid determination of cross-sectional area of anatomical structures such as blood vessels, bones and bowel, (deep within a confined surgical field) to facilitate the anastamosis of vessels, (i.e. the renal vein connection in transplantation procedures) bowel, and to locate appropriate sites for bone grafts; (3) rapid volume estimations of anatomical and pathological structures deep within a confined surgical field to clarify drainage and filling requirements (e.g. in the case of a cyst or abcess or in the case of an anurysm); to evaluate the efficacy of chemotherapy on inoperable tumors; and (4) to determine depth of surgical field and relative positions of various anatomical and pathological structures found within the field.

Many measurements made within the surgical field today, are made by an indirect method, i.e. the "two finger method". The surgeon places two fingers on either side of an anatomical structure within the field of operation. Then, while attempting to maintain them in a constant relationship, he withdraws his hand from the wound and notes the distance between his two fingers (or thumb and finger) using a straight edge rule. The disadvantages are obvious. The method (used in all types of surgery) is grossly inaccurate due to movement of the surgeon's hand; the location of the reference point on the fingers and/or thumb; and the conversion from fingers to straight edge, where the assumed reference points must necessarily still be some distance from the indicating marks upon the rule resulting in a significant parallax error.

Once these crude finger measurements have been obtained, it is necessary to incorporate them into a precise formula in order to calculate an area of cross section or the volume of the structure measured with the inevitable result of inaccuracy invalidating any attempt at procedural documentation, which is so essential for the standardization, subsequent teaching and evolution of a developed procedure.

Finally, the most important consideration, the quality of the patient's treatment is partially dependent upon the efficiency and accuracy of the operating procedure and, considering the present state of the art in surgical measuring devices, this accuracy and efficiency is completely dependent upon the surgeon's eye which is handicapped by the above discussed disadvantages.

The prior art has also described calipers of many types most of which are not useful for surgery. Many of the calipers have spaced apart projections on arms which are like curved hooks where the ends come together to provide the spaced apart projections. Illustrative are U.S. Pat. Nos. 466,986; 1,275,520; 1,719,652; 1,804,064; 1,953,498; 2,039,718; 2,456,806; 2,507,959; 2,581,219; 2,651,112; 3,740,779. U.S. Pat. No. 3,740,779 to Rubricuis describes a surgical caliper attached to a scalpel of this type for removal and then measuring of diseased veins or arteries. The risk of puncturing undamaged tissue being measured by this caliper is great and it is not suitable for use inside a body cavity.

OBJECTS

It is therefore an object of the present invention to provide a surgical caliper which gives precise, direct information regarding size, area, volume and/or depth of an anatomical or pathological structure in its perfused state, located within the surgical field (deep within the incision). It is further an object to provide an instrument which performs the measurement in less time and provides accurate documentation of surgical findings which can be reexamined during subsequent procedures, in a consistent manner to evaluate changes which may have occurred (e.g. tumor size after a period of chemotherapy). These and other objects will become increasingly apparent by reference to the following description and the drawings.

IN THE DRAWINGS

FIG. 1 is a front view of the preferred surgical caliper of the present invention particularly illustrating the closed position of the arms on a handle wherein the distal ends of the arms from the handle are adapted for measuring by means of a scale on the handle with index marks for linear measuring and a pointer which are extensions of the arms forming the handle.

FIG. 2 is an end cross-sectional view through line 2—2 of FIG. 1 illustrating one preferred construction of a pivot means.

FIG. 3 is an enlarged front view of a portion of the distal end of one of the arms of the surgical caliper of FIG. 1 particularly illustrating parallel angularly cut parabolic shaped grooves which are in precisely spaced relation along the arm in one centimeter increments.

FIG. 3a is a cross-section of the portion of the arm shown in FIG. 3.

FIG. 4 is a front view of the opposite side of the preferred surgical caliper of FIG. 1 particularly illustrating scales with index marks of precalculated formulas based upon one centimeter increments for determining volume and cross-sectional area and an indicator button on the opposite side of the extension from the pointer for rapidly visually distinguishing between the scales and showing the arms which are scissored into an open position against the pressure of a flat spring.

Figure 5:
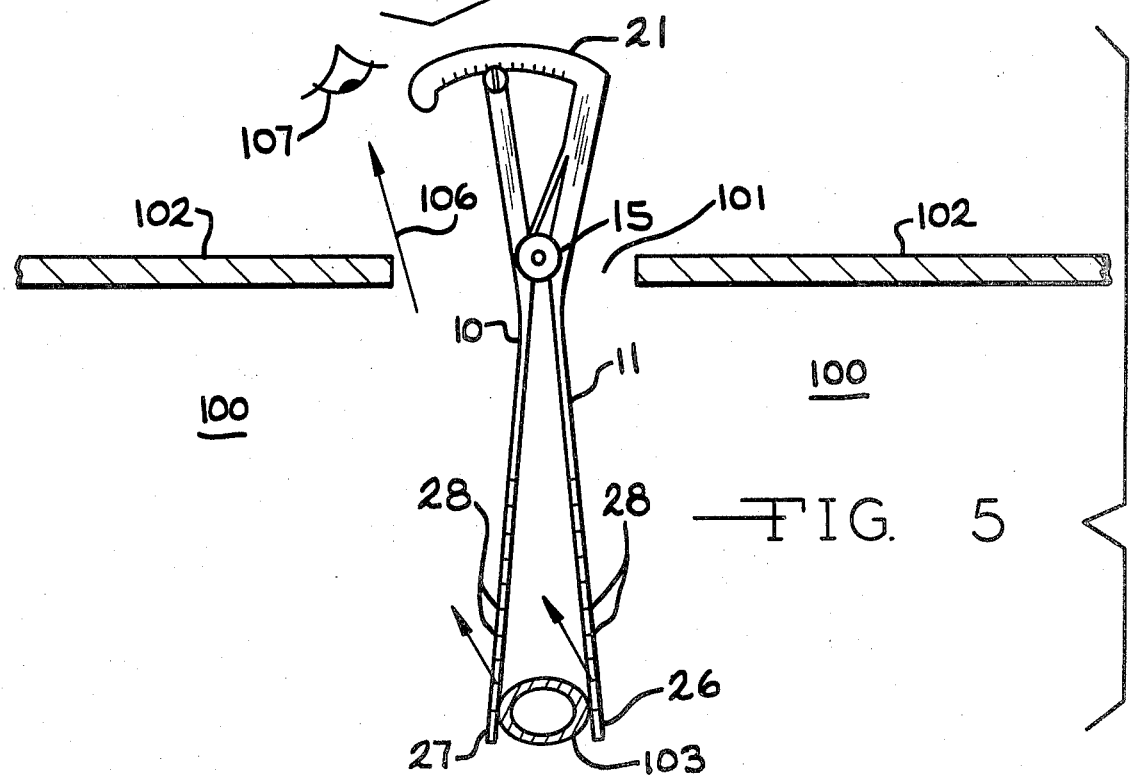

FIG. 5 is a schematic front cross-sectional view of a mammalian body cavity particularly illustrating the visible reflection from the grooves near the distal ends of the arms.

Figure 6:
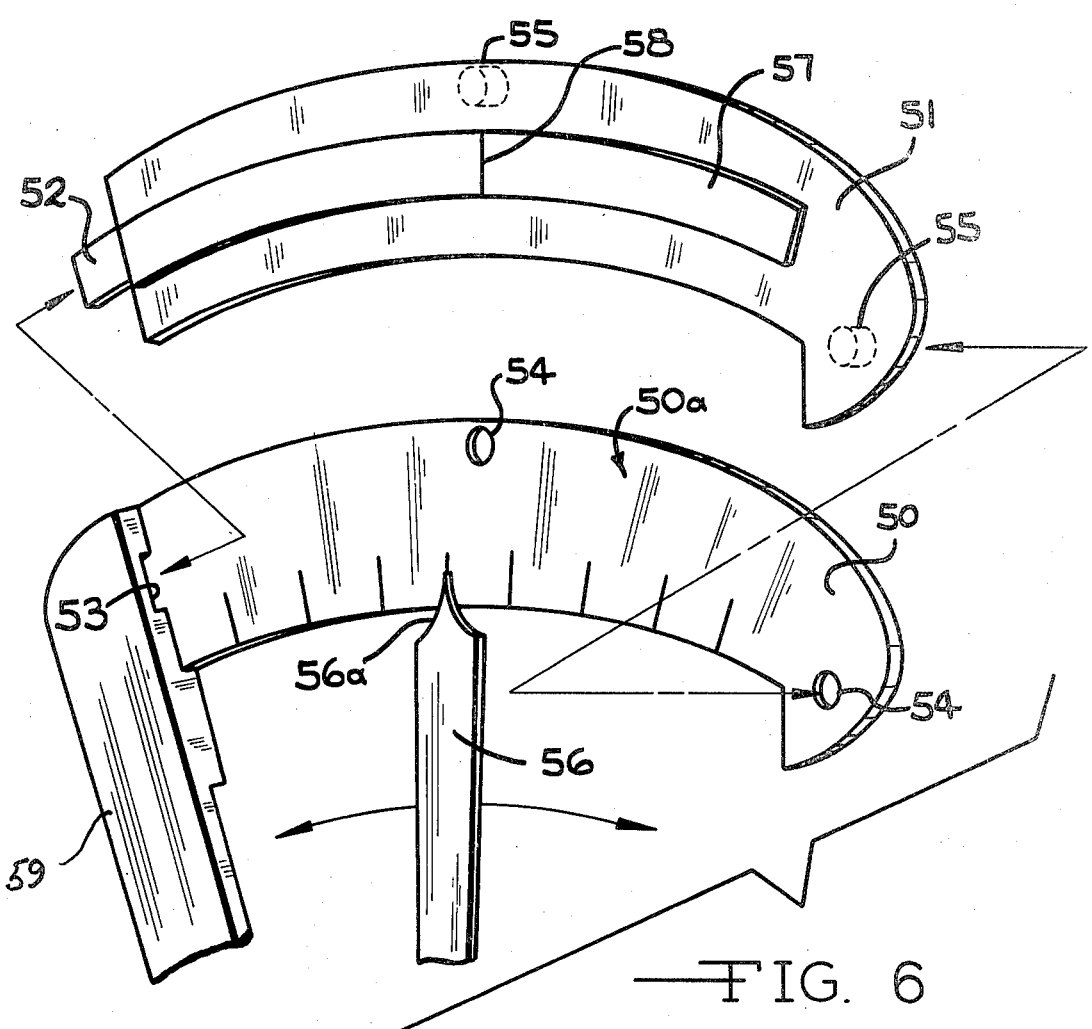

FIG. 6 is a partial section of two extensions of the arms showing a replaceable insert which is provided with a means for marking a dimension to provide a permanent record of a measurement.

GENERAL DESCRIPTION

The present invention relates to a measuring caliper adapted for measuring anatomical parts of mammals during surgery without damaging the parts particularly inside a body cavity which comprises: a pair of long straight arms with longitudinal axes which are approximately parallel in a closed position of the arms each arm having a distal end and an opposite end connected to a handle which is provided by extensions of each of the arms, the arms each having a series of parallel precisely positioned reflecting means, such as ridges or grooves, along the longitudinal axis near the distal end of the arms which can reflect light when the arms are positioned inside a body cavity for measuring; pivot means providing a pivot point between the arms and handle and joining the arms together such that the arms can open from the closed position for measuring and close in a scissors movement; and a scale with index marks as part of the handle which is attached to one of the extensions of the arms such that the other arm is moveable across the scale for measuring as the arms are opened or closed in a scissors movement. Preferably there are at least four (4) grooves or ridges on each arm.

The surgical caliper is thus constructed with the long straight arms having the light reflecting means beginning near and extending from the distal ends which are constructed so as to be easily seen inside a body cavity when measurements are taken without injury to the body part being measured. The phrase "approximately parallel" in reference to the longitudinal axes of the arms is defined to mean that the axes can converge (or diverge) slightly as shown in FIG. 1. Also the arms can taper slightly towards the distal ends of the arms as shown in FIG. 1.

SPECIFIC DESCRIPTION

Referring to FIGS. 1 and 4, the preferred surgical caliper is shown. The caliper includes two main portions, long straight arms 10 and 11, which are preferably circular in cross-section, and are attached to handle portion 12. The arms 10 and 11 have longitudinal axes 10a and 11a. The handle portion 12 includes integral extensions 13 and 14 of the arms 10 and 11 forming a "V" when the arms 10 and 11 are in the closed position shown in FIG. 1 for ease of gripping. The arms 10 and 11 and extensions 13 and 14 are pivotable on a pivot axis 15 between them. The pivot axis 15 is defined by aligned holes 18 in two spaced apart discs 16 and 17. A lip 14a is integral with the extension 14 framing a hole 14b through which a bolt 19 is fitted. A lip 13a is integral with extension 13 and a hole 13b is provided for bolt 19. The lips 13a and 14a fit together. The holes 18, 13b and 14b are aligned and bolt 19 is located through the holes 18, 13b and 14b and is held in place by threads 20 on one of the discs 16 or 17, such that the arms 10 and 11 will move in a scissors movement. The longitudinal axis of the bolt 19 is thus centered on the pivot axis 15. One extension 13 is provided with an integral flat spring 13c which contacts an inside surface 14c of the outer extension 14. The spring 13c urges the arms 10 and 11 together and the extensions 13 and 14 apart around the pivot axis 15. The extension 13 and 14 have serrations 13d and 14e for ease of gripping.

The extension 13 is provided with a scale member 21 which extends arcuately in relation to the pivot axis 15 to the other extension 14. The other extension 14 includes a pointer 14d which moves across the scale member 21 which has measuring indices or index marks 21a and 21b on both sides. The arm 13 is provided with a lip 22 or other stop means to prevent the arm 14 from moving past the indices 21a and 21b. The extension 14 is provided with the pointer 14d on one side and on the opposite side a button 23 having a gold, brass or another contrasting color for visual contrast with an aligning mark 24 which is in line with the indices 21b on the scale member 21. The button 23 also extends slightly over the surface of the scale member 21 to insure that the extension 14 and scale member 21 do not move apart.

At the distal end of the arms 10 and 11, tips 26 and 27 are provided which have a visually contrasting color, usually gold where the calipers are made of stainless steel. Adjacent the tips 26 and 27 and perpendicular to the longitudinal axes of the arms 10 and 11, are parabolic shaped grooves 28. The grooves 28 are preferably cut with rotating a disc at an angle alpha defining a parabolic axis of between about 15° to 35° to the longitudinal axes 10a and 11a of the arms 10 and 11 as shown in FIG. 3a. Preferably the angle is about 25°. The grooves 28 are polished to eliminate any sharp edges. The focal length of the parabolic grooves 28 is preferably slightly greater than two feet to make the grooves 28 easily visible. As shown in FIG. 5, the grooves 28 provide a means for easily seeing the depth of the arms 10 and 11 while they are in a body cavity 100 below an opening 101 in the skin 102 adjacent a body part 103. Light 106 such as from above an operating table (not shown) shines down on the grooves 28 which reflect the light to the eye 107 making the grooves 28 and tips 26 and 27 visibly distinct.

FIG. 6 shows a variation of a scale member 50 which is provided with a replaceable snap-on insert 51. The insert 51 has a tab 52 which fits into a recess 53 in the extension 59 supporting the member 50 which also acts as a stop for the extension 56. Pins 55 project from the insert 51 and mate with holes 54 in the arcuate member 50. The extension 56 with the point 56a is constructed so as to be above the surface 50a to provide a space d allowing for a little more than the width of the insert 51. The insert 51 is provided with an adhesively coated removeable or inscribable member or preformed sterile tape 57 which can be marked such as by mark 58 to provide a permanent record of the dimensions of a body part. The underside of the point 56a can have stylus (not shown) which can mark the tape 57 when the extension 56 is pressed with a finger or thumb. The insert and/or tape 57 can also have pre-printed index marks (not shown).

In using the surgical calipers, the arms 10 and 11 are opened by depressing extension 14 towards extension 13. The user then places gold tips 26 and 27 on either side of the anatomical or pathological structure to be measured. Then, by allowing arms 10 and 11 to lightly impinge upon the tissue surface (by releasing some of the pressure on extension 14), one notes the measurement between the gold tips 26 and 27, as a linear dimension by index marks 21a, a precalculated circular area or a precalculated spherical volume for whole 1 cm increments by indices 21b, depending on which of the marks adjacent the pointer 14d of button 23 is observed. In the preferred caliper the pointer 14d is at 0 when the arms 10 and 11 are in closed position.

For measuring depth in the surgical field, or for any measurement which can not be obtained between the tips 26 and 27, the grooves 28 on arms 10 and 11 are used by positioning the caliper so as to direct a light 106 reflecting off the grooves 28 toward the eyes 107 from the arms 10 and 11, and noting the distance in one centimeter increments relative to the distal end of the gold tips 26 and 27 which preferably comprise the first one centimeter increment. In the event of the grooves 28 being obscured, for any reason, the measurement can be obtained by noting the desired groove 28 with the end of a gloved finger and withdrawing the caliper from the field to note the measurement.

There are two aspects of the caliper which can be noted as unique and particularly suited to surgical procedure. Both pertain to the straight, preferably cylindrical, arms 10 and 11. Calipers historically have been designed with curved or hooked arms which allow precise measurements to be made between pointed tips in a point to point fashion. While this is the most precise design for obtaining caliper measurements of solid objects outside of the surgical field, it is not a safe design to use for a surgical measuring caliper, since the entire caliper closing force load is concentrated at the opposing pointed tips which could then easily penetrate a delicate body part should the instrument slip in the surgeon's hand.

In the event of a slip with the improved caliper, the danger of penetration is minimized because the force is dispersed along the arms 10 and 11 instead of only at the ends of tips 26 and 27. The closing arms 10 and 11 will deflect off the body part preventing damage. Should a slip occur while measuring a cylindrical structure (i.e. intestine), the arms 10 and 11 close upon the tissue without causing damage (due to the wide area over which the closing force had been spread).

The second aspect of the invention involves "feeling" the tissue being measured through the caliper by slightly compressing the tissue between the tips 26 and 27. This step is necessary for accurate measurements and controlled technique. The opposing tips of a curved arm instrument are inadequate in this respect. The larger area offered by the straight arms 10 and 11 enhances one's ability to "feel" the tissue through the caliper with minimum penetration worries.

Another consideration of curved arms with spaced apart points in prior art calipers is that they would not allow depth measurements to be made as with the calipers having the grooves 28 of the present invention and would limit the caliper's effectiveness in confined areas such as narrow incisions. The curved arms increase the width or spread of the arms.

The preferred reflecting means are the parabolic grooves 28; however it will be appreciated that ridges or other light reflecting surfaces can be used. The ridges are constructed so as to reflect light to the eye 107 of the surgeon when the arms 10 and 11 are inside a body cavity 100. The grooves 28 have the center 29 of the parabolic furthest from the eye 107 as the basis for determining the spacing of the grooves 28.

Structural features which are believed to be new and important are the long straight arms 10 and 11 which are preferably round to prevent damage to soft tissue structures and which allow measurements to be made within a confined surgical field, while the readout is made on an indices 21a or 21b held outside or near the opening of the surgical field which is free from blood and other fluids which might interfere with measurement. The arms 10 and 11 preferably have polished parabolic grooves 28 or ridges in one centimeter increments to best reflect the overhead lights toward the eyes of the surgeon. This facilitates measurements in the presence of blood and fluids where natural reflections cause the field to be confused.

Another preferred feature on the arms 10 and 11 are the tips 26 and 27 with a contrasting color allowing an awareness at all times, of location of the ends of the caliper. This decreases the likelihood of accidental perforation of some structure and serves to indicate where the grooves 28 on the caliper arms 10 and 11 begin.

A preferred feature on the indices 21b is an indicator in the form of a gold covered button 23 to give rapid visual awareness of the scale 21b to be used for area and/or volume determinations.

Another new feature on the extension 13 supporting the indices 21a or 21b is the capability to receive a snap-on scale 51 preferably made out of plastic or a thin piece of metal upon which can be imprinted different forms of indices or the results of previously calculated equations using various parameters besides those required for length, spherical volume or circular area. These snap-on scales 51 greatly enhance the caliper's utility in various types of surgical situations. There can also be a plastic scale with increment markings, but no marked values. This allows the surgeon to inscribe whatever notation he desires upon the scale as discussed previously.

Thus the advantages of the caliper are:

(1) Direct, precise measurements through the incision of the surgical field;

(2) Decreasing the time of an operation thereby decreasing the length of time the patient is under anesthetic (a paramount consideration in any operative procedure) by using the precalculated results which increases the efficiency and accuracy of the procedure;

(3) Versatility through the use of several scale options;

(4) Lightweight and a soft spring give the surgeon the ability to "feel" the tissues he is measuring. This allows greater accuracy in measuring and greater safety while measuring structures and tissues of very delicate nature;

(5) Precise documentation of surgical procedures for the purpose of standardization of techniques; future teaching efforts; future evaluation of results; reevaluation of pathology subsequent to chemotherapy; and (6) medical/legal documentation of surgical procedures.

Specific uses for the caliper are for instance: artery diameter for bypass procedures; cross-sectional area of renal vein in transplant work; use in all types of transplant surgery where connections to arteries, nerves, and veins must be made; establishing the size requirements of valve prosthesis in aortic valve replacement procedures; determining femoral head size in open procedures where there is to be prosthetic replacement; establishing the length of the anastomotic line in bowel surgery for medical/legal documentation; determining tumor densities; volume determinations of renal and other types of cysts; determining the efficacy of chemotherapy for inoperable cancers at the primary and subsequent surgeries; bone diameters for grafting or repair procedures; obstetrics. It has been found to be particularly effective in renal transplant procedures and a prostate volume determination prior to implantation of $I^{125}$ pellets for interstitial irradiation. Various other surgical uses will become apparent to those skilled in the art.

I claim:

1. A measuring caliper adapted for measuring anatomical parts of mammals during surgery without damaging the parts particularly inside a body cavity;

(a) a pair of long straight arms with longitudinal axes which are approximately parallel in a closed position of the arms each arm having a distal end and an opposite end connected to a handle which is provided by extensions of each of the arms, the arms each having a series of parallel precisely positioned reflecting means along the longitudinal axis near the distal end of the arms which can reflect light when the arms are positioned inside a body cavity for measuring;

(b) pivot means providing a pivot point between the arms and handles and joining the arms together such that the arms can open from the closed position for measuring and close in a scissors movement; and (c) a scale with index marks as part of the handle which is attached to one of the extensions of the arms such that the other arm extension is moveable across the scale for measuring as the arms are opened or closed in a scissors movement.

2. The caliper of claim 1 wherein the extensions of the arms together form a V shape such that the moveable arm extension is positioned at a 0 index mark on the scale when the arms are in the closed position.

3. The caliper of claims 1 or 2 wherein the arms are made of stainless steel wherein a portion of the distal ends have a contrasting colored shiny material which reflects light and provides a visual reference when the arms are inside of a body cavity.

4. The caliper of claim 1 wherein the arms are circular in cross-section.

5. The caliper of claim 1 wherein the reflecting means are grooves near the distal ends of the arms which are parabolic shaped defining a parabolic axis and center with the parabolic axis inclined towards the handle and wherein the centers of the parabolas are spaced 1 cm apart.

6. The caliper of claim 5 wherein there are at least 4 grooves in each of the arms and the parabolic axis is at an angle of between about 15° to 35° to the axis of the arm.

7. The caliper of claim 1 wherein a spring means is provided between the extensions of the arms such that the arms are urged to the closed position by the spring means and are openable by a light hand pressure.

8. The caliper of claims 1 or 2, including a spring means comprising a leaf spring provided between the arm extensions which together form a V when the arms are in a closed position such that the arms are urged to the closed position by the spring means and are openable by a light hand pressure, wherein the leaf spring is an integral part of one of the extensions which is in resilient contact with the other extension.

9. The caliper of claims 1 or 2 wherein the index marks on the scale are in an arcuate pattern such that the measuring is linear across the scale.

10. The caliper of claim 9 wherein the index marks on the scale are adapted to linear distance measurements on one side of the scale and on an opposite side of the scale to a volume measurement of an essentially spherical object and a cross-sectional area measurement of a cylindrical object.

11. The method for measuring a body part inside a body cavity in a surgical field which comprises:

(a) providing calipers with long straight arms having longitudinal axes which are approximately parallel when the arms are in a closed position and adapted for measuring at distal ends of the arms when the arms are in an open position with precisely measured spaced apart reflecting means at the distal ends of the arms, with a handle formed by two extensions of the arms at the opposite end of the arms and with at least one extension being moveable to provide a measurement on a scale;

(b) positioning the arms inside a body cavity such that the scale is outside of or near an opening in the body cavity;

(c) measuring the length of the body part in the field using the grooves; and (d) measuring the length, area or volume of a body part between the distal ends by reading the scale.

12. The method of claim 11 wherein the light reflecting means are parabolic shaped defining a parabolic axis and center with the parabolic axis inclined towards the handle at an angle of 15° to 35° to the axis of the arm and are positioned in the body cavity so as to reflect a surgical light to an eye of the user.

* * * * *